United States Patent [19]

McCarthy, Jr. et al.

[11] 3,969,532
[45] July 13, 1976

[54] 1-ARYL-3-(2-HYDROXYETHYL) THIOUREAS FOR TREATING DEPRESSION

[75] Inventors: James R. McCarthy, Jr., Midland; Don V. Wysong, Farwell; Bobbie J. Allen, Midland, all of Mich.

[73] Assignee: The Dow Chemical Company, Midland, Mich.

[22] Filed: Aug. 11, 1975

[21] Appl. No.: 603,831

Related U.S. Application Data

[62] Division of Ser. No. 438,927, Feb. 1, 1974, abandoned.

[52] U.S. Cl. .............................. 424/322; 260/552 R
[51] Int. Cl.² ........................................ A61K 31/17
[58] Field of Search ........................... 424/322, 325; 260/552 R

[56] References Cited

UNITED STATES PATENTS 3,767,816   10/1973   Moss et al ........................... 424/322

OTHER PUBLICATIONS

Chem. Abst., 55—10372f (1960).
Index Chemicus, vol. 43, Issue 41, 1971, 184408.
Chem. Abst., 55—1582d (1960).

*Primary Examiner*—Stanley J. Friedman
*Attorney, Agent, or Firm*—James W. Ambrosius; C. Kenneth Bjork

[57] ABSTRACT

Certain 1-aryl-3-(2-hydroxyethyl)thioureas which are useful as antidepressants.

2 Claims, No Drawings

1-ARYL-3-(2-HYDROXYETHYL) THIOUREAS FOR TREATING DEPRESSION

This is a division of application Ser. No. 438,927, filed Feb. 1, 1974, now abandoned.

BACKGROUND OF THE INVENTION

The present invention relates to the pharmaceutical field, and more particularly to novel 1-aryl-3-(2-hydroxyethyl)thioureas (for convenience, hereinafter referred to as "thioureas") which are useful as antidepressants.

Various 1-aryl-3-(2-hydroxyethyl)thioureas are described in the prior art. See, for example, U.S. Pat. No. 3,767,816; =French Pat. No. 1,356,908 and Schroeder, Chem. Reviews 55, 181–189 (1955). None of these references disclose the compounds of the present invention or their activity as antidepressants.

SUMMARY OF THE INVENTION

The novel compounds of the present invention may be illustrated by the formula:

$$\text{Aryl—NHCNHCH}_2\text{CH}_2\text{OH} \qquad \text{I.}$$

wherein aryl represents 2,4-dimethylbenzyl, 4-methoxy-2-methylphenyl or 2,4-dimethoxyphenyl.

The compounds of the present invention have valuable antidepressant properties at non-toxic dosage levels. Such compounds are normally crystalline solids at ambient temperatures and are ordinarily administered to mammals in doses of from about one to about fifty or move milligrams per kilogram of body weight.

DESCRIPTION OF THE PREFERRED EMBODIMENTS

The thiourea compounds are administered internally, i.e., parenterally or orally, and can be formulated into various pharmaceutical dosage forms such as tablets, capsules, solutions, suspension, pills and the like, for immediate or sustained release by combining the active compounds with suitable pharmaceutically acceptable carriers or diluents according to methods well known in the art. Such dosage forms may additionally include excipients, binders, fillers, flavoring and sweetening agents and other therapeutically inert ingredients necessary in the formulation of the desired pharmaceutical preparation.

The thioureas of the present invention provide a new class of effective antidepressants. This is surprising and unexpected since many compounds of closely related structure do not exhibit antidepressant activity. Thus, in one embodiment of the present invention, the compound of formula I wherein aryl is 2,4-dimethylbenzyl is preferred. In another embodiment of the present invention, compounds of formula I wherein aryl is 4-methoxy-2-methylphenyl or 2,4-dimethoxyphenyl are preferred.

The compounds of this invention can be prepared by the addition of ethanolamine to a selected aryl isothiocyanate reactant. The reactants are known and can be otained commercially or prepared according to known literature methods. The reaction is usually carried out by mixing the isothiocyanate reactant with a suitable reaction carrier medium, such as, for example, alcohols, benzene, acetone, dimethylformamide or other suitable carriers, and adding thereto a mixture of the ethanolamine reactant in a similar carrier. Generally, equimolar proportions of the reactants are employed. The ethanolamine reactant mixture is usually added dropwise, with agitation, to the isothiocyanate reactant mixture while maintaining the temperature of the resulting reaction mixture below about 50°C. Following the completion of the ethanolamine addition, the reaction mixture is stirred for a period of from about 1 to about 18 hours. The resulting solid product precipitate is recovered from the reaction mixture by filtration, dried, and recrystallized if desired from a suitable solvent, such as hereinbefore mentioned. Where the product precipitate is not formed in the reaction mixture, the same is concentrated by evaporation and the residue obtained is dissolved in a solvent and the solution cooled to obtain the desired product.

The following examples further illustrate the present invention.

EXAMPLE 1

1-(2,4-dimethylbenzyl)-3-(2-hydroxyethyl)thiourea 2,4-Dimethylbenzyl isothiocyanate (15.7 grams; 0.08 mole) was mixed with 23 milliliters (ml) of isopropyl alcohol and a solution of ethanolamine (5.8 grams; 0.08 mole) in 23 ml of isopropyl alcohol added dropwise thereto with stirring. The temperature of the reaction mixture was maintained below about 50°C during the ethanolamine addition and then stirred at ambient temperatures for a period of about 16 hours. The reaction mixture was then concentrated to dryness and the residue obtained taken up in benzene. The resulting benzene solution was cooled to give crystals which were filtered off. The title product was thus obtained in about a 58% yield as a crystalline solid having a melting point of 101–103°C.

EXAMPLE 2

1-(4-methoxy-2-methylphenyl)-3-(2-hydroxyethyl)thiourea

4-Methoxy-2-methylphenylisocyanate (25.7 grams; 0.14 mole) was mixed with 35 ml of isopropyl alcohol and a solution of ethanolamine (9.32 grams; 0.14 mole) in 35 ml of isopropyl alcohol added thereto dropwise over a ten minute period. During the addition, the reaction mixture temperature was maintained below about 50°C. Following the completion of the ethanolamine addition, the reaction mixture was stirred for a period of about 2 hours and then allowed to stand at ambient temperatures for a period of about 16 hours. The reaction mixture was then filtered to recover the crystalline product precipitate formed therein. The product was washed with isopropyl alcohol and dried to obtain about an 85% yield of the title compound as a lavender crystalline solid having a melting point of 171°–174°C.

In similar operations employing the procedures of Example 2 above and 2,4-dimethoxyphenylisocyanate in place of the 4-methoxy-2-methylphenylisocyanate reactant, 1-(2,4-dimethoxyphenyl)-3-(2-hydroxyethyl)thiourea was obtained in about an 82% yeild as a brown crystalline solid having a melting point of 160°–162°C.

The antidepressant properties of the compounds employed in the methods of the present invention are determined by measuring their ability to counteract ptosis induced in animals by the intraperitoneal injection of reserpine. Graded doses (from about 2.1 to about 100 mg/kg) of the active compounds of this invention are administered intraperitoneally and orally to groups of five mice each, followed 30 minutes later by an intraperitoneal injection of reserpine in an amount which is known to induce ptosis in mice. Similar groups of control mice are administered only reserpine. Forty-five minutes after the administration of reserpine, the presence or absence of ptosis is noted. The percent inhibition of ptosis is noted and the median effective dose ($ED_{50}$) of each test ingredient which protected 50% of the test mice from reserpine-induced ptosis was calculated. In such operations, the median $ED_{50}$'s were established for the compounds of the formula:

$$\text{Aryl}-\text{NH}\overset{\overset{\text{S}}{\|}}{\text{C}}\text{NHCH}_2\text{CH}_2\text{OH}$$

as set forth in the following Table.

TABLE I

| Cmpd. No. | Aryl | $ED_{50}$ i.p. | mg/kg** oral |
|---|---|---|---|
| 1. | 2,4-dimethylbenzyl | 11.0 | 6.8 |
| 2. | 4-methoxy-2-methylphenyl | 10.0 | 16.2 |
| 3. | 2,4-dimethoxyphenyl | 38.0 | — |
| 4. | *Imipramine | 15.0 | 14.0 |
| 5. | *Doxepin | 27.0 | 27.0 |

*Reference Drugs
**Calculated by the Method of Horn, Biometry 12, 311 (1956) or Litchfield and Wilcoxon, J.P.E.T., Vol. 196, No. 2 (1949).

In comparative trials employing related compounds wherein aryl is 2-methoxy and 3,4-dimethoxy, respectively, it was found that such compounds did not inhibit reserpine-induced ptosis at dosages of 60 mg/kg (i.p.).

The treatment of depression in accordance with this invention comprises administering internally to an animal a compound as represented by formula I, usually combined with a pharmaceutical excepient or carrier, in an amount sufficient to produce an antidepressant effect. Preferably, the compounds are administered orally. Advantageously, equal doses will be administered from one to six times daily.

The dosage required to achieve antidepressant activity in the animal will vary with various factors such as the species of animals, general health and tolerances of the animal, weight, sex and age of the animal, the nature and severity of the disease being treated and the like. Additionally, it is to be noted that the exact dosage of each individual compound employed in similar situations will vary. Generally, a total daily dosage would be in the range of from about 0.5 to about 100.0 or more milligrams per kilogram of body weight, usually from 1.0 to about 25.0 or more milligrams per kilogram of body weight.

The following examples are illustrative of the compounds of the present invention.

EXAMPLE 3

The following ingredients are combined:

| | Parts |
|---|---|
| 1-(2,4-dimethylbenzyl)-3-(2-hydroxy-ethyl)thiourea | 35 |
| Magnesium stearate | 5 |
| Lactose | 60 |

The combination is thoroughly milled and then screened. It is then in a form adaptable for putting into a No. 0 hard gelatine capsule.

EXAMPLE 4

The following ingredients are combined:

| | Parts |
|---|---|
| 1-(2,4-dimethoxyphenyl)-3-(2-hydoxy-ethyl)thiourea | 40 |
| Peanut oil | 60 |

The combination is thoroughly mixed into a thick slurry. It can then be put into soft gelatin capsules.

EXAMPLE 5

The following ingredients are combined:

| | Parts |
|---|---|
| 1-(4-methoxy-2-methylphenyl)-3-(2-hydoxyethyl)thiourea | 2 |
| Calcium sulfate dihydrate | 65 |
| Sucrose | 25 |
| Starch | 5 |
| Talc | 2 |
| Stearic acid | 1 |

The first three ingredients are thoroughly wet with a hot 10% gelatin solution and then dried on drying trays at about 125°F. The resulting granules are ground and then thoroughly mixed in a blending mill with the last three ingredients. The resulting powder is passed through a No. 60 mesh screen and can then be compressed into tablets.

For parenteral application these compounds can be dispersed in sterile aqueous suspension or dissolved in a pharmacologically acceptable oil or oil-water emulsion. Suitable excipients can also be added.

In view of the above, it will be seen that the several objects of the invention are achieved and other advantageous results attained.

As various changes could be made without departing from the scope of the invention it is intended that all matter contained in the above description shall be interpreted as illustrative and not in a limiting sense.

That which is claimed is:

1. A composition for treating depression in a mammal comprising an effective anti-depressant amount of the compound 1-(2,4-dimethylbenzyl)-3-(2-hydroxyethyl)thiourea in combination with a suitable pharmaceutical carrier.

2. A composition for treating depression in a mammal comprising an effective anti-depressant amount of the compound 1-(2,4-dimethoxyphenyl)-3-(2-hydroxyethyl)thiourea in combination with a suitable pharmaceutical carrier.

* * * * *